United States Patent [19]

Tsolis et al.

[11] Patent Number: 4,613,674
[45] Date of Patent: Sep. 23, 1986

[54] 2-HYDROXY-2-PHOSPHINYL ETHANALS AND 1,2-DIHYDROXY-1,2-BISPHOSPHINYL ETHANES

[76] Inventors: Alexandros K. Tsolis, 171 Old National Road, Arachovitika; Ioannis A. Mikroyannidis, Navmahias Elis 48-52, Patra, both of Greece

[21] Appl. No.: 522,866

[22] Filed: Sep. 23, 1983

Related U.S. Application Data

[62] Division of Ser. No. 288,607, Jul. 30, 1981, Pat. No. 4,431,596.

[51] Int. Cl.$^4$ .......................... C07F 9/38; C07F 9/40
[52] U.S. Cl. ................................. 558/161; 558/177; 260/502.4 P
[58] Field of Search ............... 260/946, 932, 502.4 C; 252/502.4 P; 558/161, 177

[56] References Cited

U.S. PATENT DOCUMENTS

| | | | |
|---|---|---|---|
| 2,909,559 | 10/1959 | Lanham | 260/953 |
| 3,094,549 | 6/1963 | Gurgiolo et al. | 260/953 |
| 3,214,454 | 10/1965 | Blazer et al. | 260/932 |
| 3,297,578 | 1/1967 | Crutchfield et al. | 260/502.4 P |
| 3,532,639 | 10/1970 | Hatch | 260/502.4 P |

OTHER PUBLICATIONS

Gazizov et al. "Jou. Gen. Chem. of U.S.S.R.", (English Translation/vol. 48, No. 10, p. 2154.

*Primary Examiner*—Anton H. Sutto
*Attorney, Agent, or Firm*—Stiefel, Gross, Kurland & Pavane

[57] ABSTRACT

This invention relates to novel substituted 2-hydroxy-2-phosphinyl ethanals of the general Formula I.

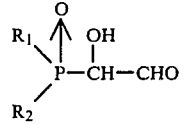

to 1,2-dihydroxy-1,2-bisphosphinylethanes of the general Formula II

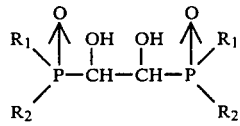

to methods of making the same, to compositions containing compounds of the general Formula I, and/or of the general Formula II, to the use of such compositions to impart flame-resistance to cellulose and cellulose containing materials, to flame-resistant compositions containing compounds of the general Formula II and to the use of the compounds of the general Formula II as metal complexing agents.

In the compounds of the Formulas I and II $R_1$ and $R_2$ may be the same or different radicals including alkoxy, aryloxy, arylalkoxy, cycloalkoxy, alkyl, alkenyl, aryl, aralkyl, cycloalkyl as well as such radicals containing substituents such as halogen, amino, hydroxy, alkoxy, mercapto, carboxy, carbalkoxy and the like in addition $R_1$ and/or $R_2$ may be hydroxy.

9 Claims, No Drawings

2-HYDROXY-2-PHOSPHINYL ETHANALS AND 1,2-DIHYDROXY-1,2-BISPHOSPHINYL ETHANES

This is a divisional of application Ser. No. 288,607, filed 7/30/81, now U.S. Pat. No. 4,431,596.

SUMMARY OF THE INVENTION

This invention relates to novel substituted 2-hydroxy ethanals containing phosphorus of the general Formula I

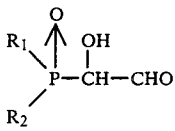

to 1,2-dihydroxy-1,2-bisphosphinylethanes of the general Formula II

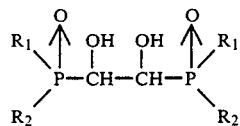

to methods of making the same, to compositions containing compounds of the general Formula I, and/or of the general Formula II, to the use of such compositions to impart flame-resistance to cellulose and cellulose containing materials, to flame-resistant compositions containing compounds of the general Formula II and to the use of the compounds of the general Formula II as metal complexing agents.

In the compounds of the Formulas I and II $R_1$ and $R_2$ may be the same or different radicals including alkoxy, aryloxy, arylalkoxy, cycloalkoxy, alkyl, alkenyl, aryl, aralkyl, cycloalkyl as well as such radicals containing substituents such as halogen, amino, hydroxy, alkoxy, mercapto, carboxy, carbalkoxy and the like in addition $R_1$ and/or $R_2$ may be hydroxy.

We have discovered that these novel compounds may be prepared in good yields by reacting glyoxal or ologomeric or polymeric compositions that may release glyoxal such as glyoxal trimer dihydrate or polyglyoxals or solutions of the above with compounds containing phosphorus of the general Formula III

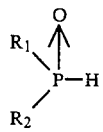

wherein $R_1$ and $R_2$ may be the same or different radicals including alkoxy, cycloalkoxy, aryloxy, arylalkoxy alkyl, alkenyl cycloalkyl, aryl, aralkyl as well as such radicals containing substituents such as halogen, amino, hydroxy, alkoxy, mercapto, carboxy, carbalkoxy and the like. The following are illustrative of the phosphorus compounds which may be employed as reactants in the procedure: dimethyl phosphite, diethyl phosphite, diisopropyl phosphite, di(n-butyl)phosphite, dicyclohexyl phosphite, diphenyl phosphite, dibenzyl phosphite di(2-chloroethyl)phosphite, methylethyl phosphite, butylphenyl phosphonite, diethylphosphine oxide, diphenylphosphine oxide. When the employed mole ratio of glyoxal to the phosphorus containing reactant is close to 1, the predominant products are the compounds of the Formula I, while when the employed mole ratio is close to 0,5, the compounds of the Formula II are obtained and they are the predominant products especially when the phosphorus containing reactant is a secondary phosphine oxide.

The reaction is carried out by contacting under stirring the reactants neat, or preferably in a reaction medium consisting of a solvent or solvent mixtures in which the reactants are at least partly soluble and by maintaining the temperature of the reaction mixture between 30° C. and 135° C. until the reaction is completed. The solvents which may be employed are: diokane, dimethylglycol, diethylglycol, acetonitrile, methanol, ethanol, propanols, butanols, dimethylformamide, dimethylsulfoxide, water, benzene, toluene etc. The choice of the solvent or the solvent mixtures will be governed by such factors as solubility of the reactants, economy for the particular application and ease of recovery of the product as well as many other considerations. In all instances, however, the solvent used should be substantially non-reactive with the reactant and the products under the prevalant reaction conditions. The acidity of the reaction mixture is governned by the acidity of the reactants being present or it may be varied as is desirable by the addition of a quantity of acid such as hydrochloric acid, sulfuric acid or the like. The preferred range of pH is between 1 and 6.

When the glyoxal releasing reactant contains water as is the case with aqueous glyoxal solution and glyoxal trimer dihydrate and when the phosphorus containing reactant is an ester, the water is preferably removed by distillation before or during the reaction under atmospheric pressure or under vacuo or azeotropically together with solvent or solvents present in the reaction mixture and/or together with part of the phosphorus containing reactant.

The novel compounds of the general Formula I and II wherein $R_1$ and/or $R_2$ are hydroxy radicals are produced by heating the compounds of general Formula I and II wherein $R_1$ and/or $R_2$ are alkoxy, arylalkoxy or aryloxy radicals in water medium or in such a medium made acidic with an acid such as hydrochloric acid. They may also be produced by hydrogenation of the compounds of the general Formula I and II wherein $R_1$ and/or $R_2$ are radicals that can undergo hydrogenolysis such as benzyloxy radicals.

The invention includes within its scope compositions of utility in imparting flame-resistance and crease-resistance to cellulose or cellulose containing materials including paper, cotton, fibers and/or fabrics, which contain at least one compound of the general formula I and/or of the general Formula II preferably of these wherein $R_1$ and $R_2$ are the same alkoxy radicals of up to four carbon atoms or such radicals containing substituents such as chlorine or bromine. Such compositions contain also an aminoplast. Preferably, such compositions also contain a latent acid catalyst to accelerate the reaction of the compound of the general Formula I and of the general Formula II with the aminoplast and/or the cellulose, curing and crosslinking of the aminoplast and its reaction products with compound of the general Formula I and of the general Formula II. The latent acid catalysts, which may be used, are well known in the process of curing aminoplasts on cellulosic materials and include for example boric acid and borax, phosphoric acid, ammonium dihydrogen orthophosphate, ammonium chloride, etc. Suitable aminoplast include condensation products of formaldeyde with urea or a derivative thereof such as ethylene urea or dihydroxyethyleneurea or, preferably, with melamine or a derivative, such as an ether of the said melamine-formaldehyde condensation product and the like. The compounds of the compositions can be employed in varying ratios and preferably in water solution or in solvent or solvent mixtures in which they are soluble and which they may not cause adverse effects to the application. A process for rendering cellulose containing materials flame-resistant and crease-resistant by treatment with such a composition followed by heating the treated material to cure the compound of general Formula I and of the general Formula II or its reaction product with the aminoplast and/or to effect crosslinking is within the scope of the invention.

The compounds of general Formula I and of the general Formula II are also useful as intermediates for the preparation of other fire retardant compounds and/or compositions, resins, plasticizers for resins and as metal complexing agents.

Within the scope of the invention are fire-resistant compositions which contain at least one compound of the general Formula II preferably of these wherein $R_1$ and $R_2$ are the same alkoxy radicals of up to four carbon atoms or such radicals containing substituents such as chlorine or bromine and polymeric materials including polyesters, polyamides, polyethylene, polystyrene.

The invention includes within its scope the use of the compounds of the general Formula II as metal complexing agents. The compounds of Formula II are generally useful as extractants of metal ions, as fuel additives, as lubricant additives, as anticorrosives, as scale removing agents. They form complexes with radioactive metal isotopes which are useful as radiopharmaceuticals. They are useful as comonomers for the production of fire-resistant polymers such as polyurethanes. The invention will be further illustrated by the following specific examples. It should be understood, however, that while these examples may describe specific features of the invention they are presented primarily for the purpose of illustration and the invention in its broader aspects is not limited thereto.

EXAMPLE 1

2-Hydroxy-2-(dimethoxyphosphinyl)ethanal and 1,2dihydroxy-1,2-bis(dimethoxyphosphinyl)ethane.

Glyoxal gas was passed through 33.3(0.30 mol) of dimethyl phosphite at 60° C. stirred in a reaction flask until 3.97 g (68.4 mmols) of glyoxal were absorbed. The reaction was exothermic and the temperature of the reaction mixture increased to 74° C. The unreacted dimethyl phosphite was distilled under vacuo and the remaining liquid product was examined by I.R., $^1$H NMR and $^{31}$P NMR spectroscopy. It was found to contain 2-ydroxy-2-(dimethoxyphosphinyl)ethanal (I.R.: C=O 1637 cm$^{-1}$; P→O 1250 cm$^{-1}$; P-O-C 1030 cm$^{-1}$) and 1,2-dihydroxy-1,2-bis(dimethoxyphosphinyl)ethane. After dilution with acetonitrile and cooling at 2° C. for 12 hr the 1,2-dihydroxy-1,2-bis(dimethoxyphosphinyl)ethane precipated as white solid: m.p. 190°–192° C. dc after recrystallization from dimethylformamide. Anal. Calcd for $C_6H_{12}O_8P_2$: C, 25.91; H, 5.80. Found: C, 26.03; H, 5.84

EXAMPLE 2

2-Hydroxy-2-(dimethoxyphosphinyl)ethanal and 1,2dihydroxy-1,2-bis(dimethoxyphosphinyl)ethane.

This is an example of the preparation of 2-hydroxy-2-(dimethoxyphosphinyl)ethanal and of 1,2-dihydroxy-1,2-bis(dimethoxyphosphinyl)ethane by reacting glyoxal trimer dihydrate with dimethyl phosphite without a solvent according to the method of the invention. Glyoxal trimer dihydrate and dimethyl phosphite in a mole ratio 0.33:1.2 respectively were introduced in a reaction flask equiped with a side condenser. The reaction mixture was heated under stirring with an oil bath maintained at 110° C. while the pressure over the reaction mixture was 80 mmHg. The released water was distilled together with a small portion of dimethyl phosphite. After a reaction time of 12 min the remaining liquid product was cooled with an ice bath. It was found by I.R., $^1$H NMR and $^{31}$P NMR spectroscopy to contain mainly 2-hydroxy-2-(dimethoxyphosphinyl)ethanal, a small amount of 1,2-dihydroxy-1,2-bis(dimethoxyphosphinyl)ethane and a minor portion of phosphate esters and phosphorus containing acids arising from isomerization and hydrolysis of the above mentioned products and of the starting material.

EXAMPLE 3

2-Hydroxy-2-(dimethoxyphosphinyl)ethanal and 1,2dihydroxy-1,2-bis(dimethoxyphosphinyl)ethane.

This is an example of the preparation of 2-hydroxy-2(dimethoxyphosphinyl)ethanal and of 1,2-dihydroxy-1,2-bis(dimethoxyphosphinyl)ethane according to the method of the invention. Glyoxal trimer dihydrate and dimethyl phosphite in a mole ratio 0.33:2.2 respectively were introduced in a reaction flask equiped with a side condenser. The reaction mixture was heated under stirring with an oil bath maintained at 130° C., while the pressure over the reaction mixture was maintained at 80 mmHg. The released water was distilled together with a small portion of dimethyl phosphite in a slow rate. After a reaction time of 12 min the remaining liquid product was cooled with an ice bath. It was shown spectroscopically to contain 2-hydroxy-2-(dimethoxyphosphinyl)ethanal, and 1,2-dihydroxy-1,2-bis(dimethoxyphosphinyl)thane. Dilution with acetonitrile and cooling at 2° C. for 12 h caused the precipitation of 1,2-dihydroxy-1,2-bis(dimethoxyphosphinyl)ethane as a white solid: m.p. 190°–192° C. dc after recrystallization from dimethylformamide. Anal. Calcd for $C_6H_{16}O_8P_2$: C, 25.91; H 5.80. Found: C, 26.08; H, 5.85.

EXAMPLE 4

2-Hydroxy-2-(diethoxyphosphinyl)ethanal and 1,2dihydroxy-1,2-bis(diethoxyphosphinyl)ethane.

Glyoxal gas was passed through 41.5 g (0.30 mol) of diethyl phosphite at 60° C. stirred in a reaction flask until 4.0 g of glyoxal were absorbed. The reaction was exothermic and the temperature of the reaction mixture increased to 76° C. The unreacted diethyl phosphite was removed under vacuo and the remaining liquid product was examined by I.R., $^1$H NMR and $^{31}$P NMR spectroscopy. It was found to contain 2-hydroxy-2-(diethoxyphosphinyl)ethanal (I.R.: C=O 1637 cm$^{-1}$; P→O 1250 cm$^{-1}$; P-O-C 1030 cm$^{-1}$. $^{31}$P NMR: $\delta = -11,9$ ppm) and 1,2-dihydroxy-1,2-bis(diethoxyphosphinyl)ethane which upon dilution of the reaction mixture with ether precipitated as a white solid: m.p. 175°–177° C. after recrystallization from dioxane. Anal. Calcd for $C_{10}H_{24}O_8P_2$: C, 35.93; H, 7.24. Found: C, 35.64; H, 7.03. $^{31}P$ NMR: $\delta = -27.3$ ppm.

EXAMPLE 5

2-Hydroxy-2-(diethoxyphosphinyl)ethanal and 1,2-dihydroxy-1,2-bis(diethoxyphosphinyl)ethane.

This is an example of the preparation of 2-hydroxy-2-(diethoxy phosphinyl)ethanal and 1,2-dihydroxy-1,2-bis(diethoxyphosphinyl)ethane by reacting glyoxal trimer dihydrate with diethyl phosphite according to the method of the invention. Glyoxal trimer dihydrate and diethyl phosphite in a mole ratio 0.33:1.2 respectively were introduced in a reaction flask equiped with a side condenser. The reaction mixture was heated under stirring with an oil bath maintained at 125° C. while the pressure over the reaction mixture was maintained at about 80 mmHg. The released water was distilled together with a small amount of diethylphosphite in a slow rate. After a reaction time of 8 min the remaining viscous liquid product was cooled with an ice bath. It was found by I.R., $^1H$ NMR, and $^{31}P$ NMR spectroscopy that it consisted mainly (70%) of 2-hydroxy-2-(diethoxyphosphinyl)ethanal ($^{31}P$ NMR $\delta = -11,9$ ppm), a small amount of 1,2-dihydroxy-1,2-bis(diethoxyphosphinyl)ethane($^{31}P$ NMR $\delta = -27.3$ ppm) the rest being phosphate esters and phosphorus containing acids arising from isomerization and hydrolysis of the above mentioned products and of the starting material.

EXAMPLE 6

2-Hydroxy-2-(diethoxyphosphinyl)ethanal and 1,2-dihydroxy-1,2-bis(diethoxyphosphinyl)ethane.

This is an example of the preparation of 2-hydroxy-2-(diethoxyphosphinyl)ethanal and 1,2-dihydroxy-1,2-bis(diethoxyphosphinyl)ethane according to the method of the invention. Glyoxal trimer dihydrate and diethylphosphite in a mole ratio 0.33:2.2 respectively were introduced in a reaction flask equiped with a side condenser. The reaction mixture was heated under stirring with an oil bath maintained at 130° C. while the pressure over the reaction mixture was maintained at about 80 mmHg. The released water was distilled together with a small portion of diethyl phosphite in a slow rate. After a reaction time of 10 min the remaining liquid product was shown spectroscopically that it contained 2-hydroxy-2-(diethoxyphosphinyl)ethanal and 1,2-dihydroxy-1,2-bis(diethoxyphosphinyl)ethane. Dilution with ether and cooling at 2° C. for 12 hr caused the precipitation of 1,2-dihydroxy-1,2-bis(diethoxyphosphinyl)ethane as a white solid: m.p. 175°–177° C. after recrystallization from dioxane.

EXAMPLE 7

2-Hydroxy-2-(diethoxyphosphinyl)ethanal and 1,2-dihydroxy-1,2-bis(diethoxyphosphinyl)ethane.

This is an example of the preparation of 2-hydroxy-2-(diethoxyphosphinyl)ethanal and of 1,2-dihydroxy-1,2-bis(diethoxyphosphinyl)ethane by reacting trimer dihydrate and diethylphosphite in dioxane. Glyoxal trimer dihydrate and diethylphosphite in a mole ratio 0.33:1.1 respectively together with 750 ml dioxane per mol of glyoxal trimer dihydrate were introduced in a reaction flask equiped with a side condenser. The reaction mixture was heated under stirring with an oil bath for 35 min., during which time the released water was distilled together with dioxane at atmospheric pressure in a slow rate. The reaction mixture was cooled to 40° C. and the volatite components were removed by a rotary evaporator at this temperature. The remaining liquid product consisted of 2-hydroxy-2-(diethoxyphosphinyl)ethanal of 1,2-dihydroxy-1,2-bis(diethoxyphosphinyl)ethane and of minor amounts of isomerization and hydrolysis products.

EXAMPLE 8

2-Hydroxy-2-(diethoxyphosphinyl)ethanal and 1,2-dihydroxy-1,2-bis(diethoxyphosphinyl)ethane.

This is an example of the preparation of 2-hydroxy-2-(diethoxyphosphinyl)ethanal and 1,2-dihydroxy-1,2-bis(diethoxyphosphinyl)ethane by the reaction of aqueous glyoxal and diethyl phosphite according to the method of the invention. The water was removed from a 30% aqueous solution of glyoxal by a rotary evaporator at 50° C. The remaining liquid was diluted with 250 ml dioxane per mol glyoxal and 1.1 mol of diethyl phosphite per mol of glyoxal was added to the solution. The reaction mixture was heated in a reaction flask equiped with a side condenser for 35 min, during which time the remaining water and dioxane were distilled at atmospheric pressure. Te reaction mixture was cooled to 40° C. and the volatile components were removed by a rotary evaporator at this temperature. The remaining liquid product consisted of 2-hydroxy-2-(diethoxyphosphinyl)ethanal, of 1,2-dihydroxy-1,2-bis(diethoxyphosphinyl)ethane and and a small amount of phosphate esters arising from isomerization and hydrolysis as shown spectroscopically.

EXAMPLE 9

2-Hydroxy-2-(diethoxyphosphinyl)ethanal and 1,2-dihydroxy-1,2-bis(diethoxyphosphinyl)ethane.

In this Example the general procedure of Example 7 was followed with the exception that the solvent was ethanol and the reaction time 150 min. The obtained products were 2-hydroxy-2-(diethoxyphosphinyl)ethane and small amount of phosphate esters from isomerizations as shown spectroscopically.

EXAMPLE 10

2-Hydroxy-2-(diethoxyphosphinyl)ethanal and 1,2-dihydroxy-1,2-bis(diethoxyphosphinyl)ethane.

In this Example the general procedure of Example 7 was followed with the exception that the solvent was toluene and the reaction time 30 min. The reaction product contained 2-hydroxy-2-(diethoxyphosphinyl)ethanal and 1,2-dihydroxy-1,2-bis(diethoxyphosphinyl)ethane.

EXAMPLE 11

2-Hydroxy-2-(diisopropoxyphosphinyl)ethanal and 1,2-dihydroxy-1,2-bis(diisopropoxyphosphinyl)ethane.

This Example demonstrates the preparation of 2-hydroxy-2-(diisopropoxyphosphinyl)ethanal and of 1,2-dihydroxy-1,2-bis(diisopropoxyphosphinyl)ethane by the method of the invention. In this Example the general procedure of Example 2 was followed with the exception that the reaction temperature was 130° C. and the reaction time 30 min. As shown spectroscopically the liquid product contained 2-hydroxy-2-(diisopropoxyphosphinyl)ethanal and 1,2-dihydroxy-1,2-bis(diisopropoxyphosphinyl)ethane. After addition of ether to the reaction product and cooling at 2° C. for 12 h a white solid precipitated and was proved to be 1,2-dihydroxy-1,2-bis(diisopropoxyphosphinyl)ethane: m.p. 186°–188° C. after recrystallization from acetonitrile chloroform 6:1, V:V. Anal. Calcd for $C_{14}H_{32}O_8P_2$: C, 43.07, H, 8.26. Found: C, 42.98, H, 8.32.

EXAMPLE 12

2-hydroxy-2-(diisopropoxyphosphinyl)ethanal and 1,2-dihydroxy-1,2-bis(diisopropoxyphosphinyl)ethane.

For the preparation of 2-hydroxy-2-(diisopropoxyphosphinyl)ethanal and 1,2-dihydroxy-1,2-bis(diisopropoxyphosphinyl)ethane glyoxal trimer dihydrate reacted with diisopropyl phosphite for 55 min in dioxane according to the general procedure of the Example 7. The viscous reaction product, as shown spectroscopically, contained mainly 2-hydroxy-2-(diisopropoxyphosphinyl)ethanal and 1,2-dihydroxy-1,2-bis(diisopropoxyphosphinyl)ethane and a minor amount of phosphates and phosphorus containing acids arising from isomerization and hydrolysis of the above mentioned products and of the starting material.

EXAMPLE 13

2-Hydroxy-2-(diisopropoxyphosphinyl)ethanal and 1,2-dihydroxy-1,2-bis(dimethoxyphosphinyl)ethane.

This Example demonstrates the preparation of 2-hydroxy-2-(diisopropoxyphosphinyl)ethanal and 1,2-dihydroxy-1,2-bis(diisopropoxyphosphinyl)ethane by the method of the invention. In this Example the general procedure of the Example 3 was followed with the exception that the reaction time was 35 min. The liquid product was shown spectroscopically that it contained 2-hydroxy-2-(diisorpopoxyphosphinyl)ethanal and 1,2-dihydroxy-1,2-bis(diisopropoxyphosphinyl)ethane, which precipitated as a white solid by dilution of the reaction product with ether and by cooling at 2° C. for 12 h. After recrystallization from acetonitrile chloroform 6:1, V:V m.p. 186°–188° C., It analyzed correctly for $C_{14}H_{32}O_8P_2$.

EXAMPLE 14

2-Hydroxy-2-[di(n-butoxy)phosphinyl]ethanal and 1,2-dihydroxy-1,2-bis[di(n-butoxy)phosphinyl]ethane.

This Example demonstrates the preparation of 2-hydroxy-2-(di-n-butoxyphosphinyl)ethanal and of 1,2-dihydro-1,2-bis(di-n-butoxyphosphinyl)ethane by the method of the invention. The general procedure of Example 2 was followed with the exception that the reaction temperature was 130° C. and the reaction time 30 min. The reaction product contained 2-hydroxy-2-[di(n-butoxy)phosphinyl]ethanal and 1,2-dihydroxy-1,2-bis[di(n-butoxy)phosphinyl]ethane as shown spectroscopically. After dilution with ether and cooling for 12 hr the 1,2-dihydroxy-1,2-bis[di(n-butoxy)phosphinyl]ethane precipitated as white solid: m.p. −172° C. after recrystallization from acetonitrile. Anal. Calcd for $C_{18}H_{40}O_8P_2$: C, 48.42; H, 9.03. Found: C, 48.26; H, 8.82.

EXAMPLE 15

2-Hydroxy-2-[di(n-butoxy)phosphinyl]ethanal and 1,2-dihydroxy-1,2-bis[di(n-butoxy)phosphinyl]ethane.

For the preparation of 2-hydroxy-2-[di(n-butoxy)phosphinyl]ethanal and 1,2-dihydroxy-1,2-bis[di(n-butoxy)phosphinyl]ethane glyoxal trimer dihydrate reacted with di(n-butyl)phosphite for 60 min in dioxane according to the general procedure of the Example 7. The reaction product consisted mainly of 2-hydroxy-2-di n-butoxyphosphinyl ethanal and of 1,2-dihydroxy 1,2-bis[di(n-butoxy)phosphinyl]ethane as shown spectroscopically. Upon dilution with ether the 1,2-dihydroxy-1,2-bis[di(n-butoxy)phosphinyl]ethane precipitated as a white solid: m.p. 170°–172° C. after recrystallization from acetonitrile. It analyzed correctly for $C_{18}H_{40}O_8P_2$.

EXAMPLE 16

2-Hydroxy-2-[di(2-chloroethoxy)phosphinyl]ethanal and 1,2-dihydroxy-1,2-bis[di(2-chloroethoxy)phosphinyl]ethane.

This is an Example of the preparation of 2-hydroxy-2-[di(2-chloroethoxy)phosphinyl]ethanal and 1,2-dihydroxy-1,2-bis(di[2-chloroethoxy)phosphinyl]ethane according to the method of the invention. Glyoxal trimer dihydrate and di(2-chloroethyl)phosphite in a mole ratio 0.33:2.2 respectively together with 300 ml of dioxane per mole of glyoxal trimer dihydrate were introduced into a reaction flask equiped with a side condenser. The reaction mixture was heated under stirring with an oil bath for 55 min during which time the released water was distilled together with dioxane at atmospheric pressure. At the end of the reaction the volatile components were removed by aspirator vacuum by a rotary evaporator. The remaining viscous liquid product contained 2-hydroxy-2-[di(chloroethoxy)phosphinyl]ethanal and 1,2-dihydroxy-1,2-bis[di(2-chloroethoxy)phosphinyl]ethane as shown spectroscopically. Dilution with acetonitrile and cooling at 2° C. for 12 h caused the precipitation of 1,2-dihydroxy-1,2-bis[di(2-chloroethoxy)phosphinyl]ethane as a white solid: m.p. after recrystallization from dimethylsulfoxide 195°–197° C. Anal. Calcd for $C_{10}H_{20}Cl_4O_8P_2$: C, 25.44; H, 4.27. Found: C, 25.76; H, 4.29.

EXAMPLE 17

2-Hydroxy-2-[di(2-chloroethoxy)phosphinyl]ethanal and 1,2-dihydroxy-1,2-bis[di(2-chloroethoxy)phosphinyl]ethane.

For the preparation of 2-hydroxy-2-[di(2-chloroethoxy)phosphinyl]ethanal and 1,2-dihydroxy-1,2-bis[di(2-chloroethoxy)phosphinyl]ethane glyoxal trimer dihydrate reacted for 25 min with di(2-chloroethyl)phosphite in dioxane according to the general procedure of Example 7. The liquid reaction product contained mainly 2-hydroxy-2-(2-chloroethoxy)phosphinyl)ethanal and 1,2-dihydroxy-1,2-bis[di(2-chloroethoxy)phosphinyl]ethane as shown spectroscopically.

EXAMPLE 18

2-Hydroxy-2-(dibenzyloxyphosphinyl)ethanal and 1,2-dihydroxy-1,2-dihydroxy-1,2-bis(dibenzyloxyphosphinyl)ethane.

For the preparation of 2-ydroxy-2(dibenzyloxyphosphinyl)ethanal and 1,2-dihydroxy-1,2-bis(dibenzyloxyphosphinyl)ethane glyoxal trimer dihydrate reacted with dibenzyl phosphite according to the procedure of example 16 with the exception that the reaction time was 20 min. It was shown spectroscopically that the liquid reaction product contained 2-hydroxy-2-(dibenzyloxyphosphinyl)ethane and 1,2-dihydroxy-1,2-bis(-dibenzyloxyphospinyl)ethane. Addition of ether and cooling at 2° C. for 12 h caused the precipitation of 1,2-dihydroxy-1,2-bis(dibenzyloxyphosphinyl)ethane as a white solid: m.p. 190°–192° (after recrystallization from chloroform Anal. Calcd for $C_{30}H_{32}\ _8P_2$: C, 61.85; H, 5.54. Found: C, 61.75; H 5.70.

EXAMPLE 19

2-hydroxy-2-(dicyclohexyloxyphosphinyl)ethanal and of 1,2-dihydroxy-1,2-bis(dicyclohexyloxyphosphinyl)ethane.

For the preparation of 2-hydroxy-2-(dicyclohexyloxyphosphinyl)ethanal and 1,2-dihydroxy-1,2-bis(dicyclohexyloxyphosphinyl)ethane glyoxal timer dihydrate reacted with dicyclohexyl phosphite for 90 min according to the general procedure of Example 7. It was shown spectroscopically that the viscous liquid reaction product, contained mainly 2-hydrxy-2-(dicycloexyloxyphosphinyl)ethanal and 1,2-dihydroxy-1,2-bis(dicyclohexyloxyphosphinyl)ethane. Addition of ether and cooling at 2° C. for 12 h caused the precipitation of 1,2-dihydroxy-1,2-bis(dicyclohexyloxyphosphinyl)ethane as a white solid:m.p.209°–210° C. dcn after recrystallization from dimethylformamide. Anal. Calcd for $C_{26}H_{48}O_8P_2$: C,56.71; H 8.79. Found: C,56,84; H, 8.33.

EXAMPLE 20

2-hydroxy-2-(diphenoxyphosphinyl)ethanal and 1,2-dihydroxy 1,2-bis(diphenoxyphosphinyl)ethane.

This is an example of the preparation of 2-hydroxy-2-(diphenoxyphosphinyl)ethanal and 1,2-dihydroxy-1,2-bis(diphenoxyphosphinyl)ethane by the method of the invention. 7.0 g(0.003 mol) of glyoxal trimer dihydrate and 51.5 g(0.22 mol) of diphenyl phosphite were introduced in a reaction flask equiped with a side condenser. The reaction mixture was heated under stirring with an oil bath maintained at 80° C. for 50 min during which time the released water together with a small portion of phosphite were distilled in a slow rate under aspirator vacuo. It was shown spectroscopically that the remaining liquid product contained mainly 2-hydroxy-2(diphenoxyphosphinyl)ethanal and 1,2-dihydroxy-1,2-bis(diphenoxyphosphinyl)ethane which precipitated after dilution with acetone and cooling at 2° C. as a white solid: m.p. 208°–209° C. after recrystallization from dioxane. Anal. Calcd for $C_{26}H_{24}O_8P_2$: C, 59.32; H, 4.60. Found: C, 59.12; H, 4.50.

EXAMPLE 21

2-Hydroxy-2-(n-butoxyphenylphosphinyl)ethanal and 1,2-dihydroxy-1,2-bis(n-butoxyphenylphosphinyl)ethane.

This is an example of the preparation of 2-hydroxy-2-(n-butoxyphenylphosphinyl)ethanal and 1,2-dihydroxy-1,2-bis(n-butoxyphenylphosphinyl)ethane according to the method of the invention. Glyoxal trimer dihydrate and O-n-butylphenylphosphonite in a molratio o,33:1 respectively together with 750 ml of dioxane per mol of glyoxal trimer dihydrate were introduced in a reaction flask equiped with a side condenser. The reaction mixture was heated under stirring with an oil bath at 110° C. for 20 min during which time the released water was distilled together with dioxane at atmospheric pressure in a slow rate. The remaining reaction mixture was cooled to 40° C. and its volatile components were removed by a rotary evaporator at this temperature and at 12 mmHg. It was shown spectroscopically that the remaining viscous liquid product contained mainly 2-hydroxy-2-(n-butoxyphenylphosphinyl)ethanal and 1,2-dihydroxy-1,2-bis(n-butoxyphenylphosphinyl)ethane, which precipitated after addition of ether and cooling at 2° C. for 12 h as a white solid:m.p.190°–192° C. after recrystallization from chloroform-acetonitrile 3:1,V:V. Anal. Calcd for $C_{22}H_{32}O_6P_2$: C, 58.19; H, 7.09. Found: C, 58.10; H, 7.07.

EXAMPLE 22

1,2-Dihydroxy-1,2-bis(diethylphosphinyl)ethane.

This is an example of the preparation of 1,2-dihydroxy-1,2-bis(diethylphosphinyl)ethane by the method of the invention. 2.1 g of 30% aqueous glyoxal solution (15 mmols glyoxal), 3.18 g(30 mmols) of diethylphosphine oxide and 10 ml of water were introduced into a round bottom flask. The initial pH of the reaction mixture was 2. Evolution of heat was observed. The reaction mixture was heated for 30 min at 50° C. Cooling at 2° C. caused the precipitation of 1,2-dihydroxy-1,2-bis(diethylphosphinyl)ethane m.p. 181°–183° C. after recrystallization from acetonitrile-chloroform 2:1, V:V. Anal. Calcd for $C_{10}H_{24}O_4P$: C, 44.44; H, 8.95. Found: C, 44.53; H. 8.95.

EXAMPLE 23

1,2-Dihydroxy-1,2-bis(diphenylphosphinyl)ethane.

7.73 g of 30% aqueous glyoxal solution (40 mmols glyoxal), 16.17 g (80 mmols) of diphenylphosphine oxide and 40 ml of benzene were introduced into a round bottom flask. The initial pH of the reaction mixture was heated for 30 min with a water bath at 40° C. The precipitated white product was separated by filtration and weighed 16.64 g (90% yield) m.p. 211°–214° C. After recrystallization from dimethylsulfoxide-acetonitrile 3:2, V:V gave a sample of 1,2-dihydroxy-1,2-bis(diphenylphosphinyl)ethane m.p. 216°–217° C. Anal. Calcd for $C_{26}H_{24}O_4P_2$: C, 67.53; H, 5.23. Found: C, 67.42; H, 5.34.

EXAMPLE 24

1,2-Dihydroxy-1,2-bis(dihydroxyphosphinyl)ethane.

This example demonstrates the preparation of 1,2-dihydroxy-1,2-bis(dihydroxyphosphinyl)ethane by hydrolysis of 1,2-dihydroxy-1,2-bis(dialkoxyphosphinyl)ethane according to the method of the invention. A 0.18 molar solution of 1,2-dihydroxy-1,2-bis(diethoxyphosphinyl)ethane in 37% hydrochloric acid was refluxed for three hours. After the removal of the volatile components of the mixture under vacuo a nearly quantitive yield of 1,2-dihydroxy-1,2-bis(dihydroxyphosphinyl)ethane was obtained: m.p. 209°–211° C. after recrystallization from methanol-ether 8:2, V:V. It analyzed correctly for $C_2H_8O_8P_2$.

EXAMPLE 25

1,2-Dihydroxy-1,2-bis(dihydroxyphosphinyl)ethane.

This example demonstrates the preparation of 1,2-dihydroxy-1,2-bis(dihydroxyphosphinyl)ethane by hydrolysis of 1,2-dihydroxy-1,2-bis(diaryloxyphosphinyl)ethane according to the method of the invention. The procedure of the example 24 was followed with the exception that a dispersion of 1,2-dihydroxy-1,2-bis(diphenoxyphosphinyl)ethane was refluxed in 10% hydrochloric acid. A nearly quantitative yield of 1,2-dihydroxy-1,2-bis(dihydroxyphosphinyl)ethane was obtained.

EXAMPLE 26

1,2-Dihydroxy-1,2-bis(dihydroxyphosphinyl)ethane.

This example demonstrates the preparation of 1,2-dihydroxy-1,2-bis(dihydroxyphosphinyl)ethane by hydrogenation of 1,2-dihydroxy-1,2-bis(dibenzyloxyphosphinyl)ethane according to the method of the invention.

202 mg of recrystallized 1,2-dihydroxy-1,2-bis(dibenzyloxyphosphinyl)ethane and 20 ml of methanol was introduced in an hydrogeneration flask together with the catalyst, 10% palladium on carbon, and hydrogenaration was carried out under atmospheric pressure and under stirring of the dispersion until no more hydrogen was uptaken. 31.77 cm$^3$ of hydrogen at STP were uptaken by the mixture. The initially heterogeneous mixture was turned into solution. After the filtration of the catalyst and the removal of the volatile components under vacuo a nearly quantitative yield of 1,2-dihydroxy-1,2-bis(dihydroxyphosphinyl)ethane was obtained: m.p. 209°–211° C. after recrystallization from methanol-ether 8:2, V:V. Anal. Calcd for $C_2H_8O_8P_2$: C, 10.82; H, 3.63. Found: C, 11.05; H, 3.42.

EXAMPLE 27

The organophosphorus compounds of the general Formula I and of the general Formula II of the present invention are useful as fire retardants. The following examples illustrate some of the uses of typical products.

Examples of fire retardant and crease improving compositions and of a finishing procedure of cotton fabrics are reported below:

The fire retardant and crease improving compositions are prepared by mixing 15 parts of the products of one of the Examples described above, 45 parts of 40% aqueous solution of trimethylolmelamine, 39 parts of an aqueous solution containing 3.5% borax and 1.5% boric acid and 1 part of surfactant.

An example of a finishing procedure and of the testings is described below: Specimens of cotton fabric are padded into the finishing composition to a certain weight increase dried by a stream of hot air at 80° C. and then cured at 160° C. for 10 min. The specimens are then washed for 10 min at 60° C. with a 20% aqueous sodium bicarbonate solution, rinsed with water and dried. The flame resistance of the specimens was tested by AATCC-34-1966 method. The crease resistance was determined by the AATCC 66-1975 method and the breaking load according to the ASTM method D 1682-64. The unfinished cotton fabric had the following characteristics: weight 122 g/m$^2$, recovery angle 161°; breaking load of the specimens cut parallely to the warp yarns 65 kg/cm and of the specimens cut parallely to the weft yarns 35 kg/cm. The characteristics of the specimens of the above cotton fabric finished according to the above procedure with the product of the Example 2 and of the Example 7 and of the Example 17 are reported in Table I.

TABLE I

| | | Pick up of | | | |
|---|---|---|---|---|---|
| Product of the Example | Specimen | finishing composition % | Char length (cm) | Recovery angle (degrees) | Breaking load (kg/cm) |
| 2 | warp | 110 ± 3 | 8.7 ± 0.2 | 236 ± 3 | 43 ± 2 |
| | weft | 114 ± 3 | 7.1 ± 0.4 | 238 ± 4 | 22 ± 3 |
| 7 | warp | 121 ± 3 | 7.9 ± 0.5 | 222 ± 3 | 37 ± 2 |
| | weft | 118 ± 2 | 8.1 ± 0.5 | 228 ± 2 | 11 ± 2 |
| 17 | warp | 112 ± 1 | 7.7 ± 0.6 | 257 ± 2 | 37 ± 2 |
| | weft | 112 ± 1 | 8.0 ± 02 | 255 ± 3 | 16 ± 1 |

Characteristics of cotton fabric finished with typical products of the present invention An example of fire retardant composition and of a procedure of treatment of paper wheet with this composition is reported below:

The fire retardant composition is prepared by mixing 14 parts of the product of one of the Examples of the present invention, 10 parts of urea and 76 parts of water.

The procedure of treatment comprises padding the paper sheet to a certain weight increase and drying. For the purpose of illustration theresults of the treatment of paper sheet specimens of various weights with the product of Example 7 are reported in Table II. The char lengths of the treated specimens were determined by the method AATCC 34-1966.

TABLE II

Char lengths of paper sheets treated with the product of the Example 7.

| Weight of the unfinished paper sheet (g/m$^2$) | Pick up (%) | Char length (cm) |
|---|---|---|
| 200 | 100.0 | 12.0 |
| " | 108.9 | 10.5 |
| 240 | 87.8 | 13.0 |
| " | 97.8 | 10.7 |
| " | 101.6 | 10.3 |
| " | 121.3 | 9.2 |
| 280 | 99.6 | 10.7 |
| " | 106.6 | 10.0 |
| " | 113.6 | 9.4 |
| " | 118.2 | 9.0 |

The compounds of the general Formula II are useful as additives or as comonomers for the preparation of fire resistant compositions. These uses are demonstrated by the following examples:

Powder of 1,2-dihydroxy-1,2-bis(dimethoxyphosphinyl)ethane was mixed with powders of Nylon-66, polyethylene and polystyrene in the percentages shown in Table III. The Limiting Oxygen Index of the specimens formed by hot pressing in a mold were determined by the method ASTM D 2863-70 and showed that the blends had increased fire resistance in comparison to the neat polymers as shown in Table III.

TABLE III

Fire resistant polymer blends containing 1,2-dihydroxy-1,2-bis(dimethoxyphosphinyl)ethane.

$(CH_3O)_2P(O)CH-OH$
$(CH_3O)_2P(O)CH-OH$

| % in blend | Limiting Oxygen Index of the blend with: | | |
|---|---|---|---|
| | Nylon 66 | Polyethylene | Polystyrene |
| 0 | 23.2 | 18.7 | 18.7 |
| 5 | 26.0 | 21.2 | 21.9 |
| 10 | 27.1 | 22.5 | 23.1 |
| 15 | 28.1 | 23.2 | 23.9 |
| 20 | 28.7 | 23.4 | 24.7 |
| 25 | 28.9 | 23.5 | 25.5 |

1,2-dihydroxy-1,2-bis(diethoxyphosphinyl)ethane was copolymerized with ethyleneglycol and 2,4-tolylene diisocyanate so that the urethane produced contained 2,48% P by weight. The Limiting Oxygen Index of the urethane product determined by the method ASTM D 2863-70 was found to be 26,9 versus 22,4 for the regular poly(ethylene-2,4-tolylene urethane).

The compounds of general formula II are useful as metal complexing agents. The following example demonstrates their metal complexing ability.

0.20 g (0.6 mmol) of 1,2-dihydroxy-1,2-bis(diethoxyphosphinyl)ethane dissolved in 5 ml of absolute ethanol was mixed with a solution of 0.16 g (1.2 mmols) of anhydrous copper chloride in 5 ml of absolute ethanol.

The obtained solution was stirred at room temperature for 30 min. Upon addition of absolute ether a nearly quantitative yield of a complex was obtained which did not melt up to 270° C. and which showed the following I.R. absorption bands: 3.15, 8.10, 9.23, 9.65, 10.10 and 12.02 μm.

It should be understood that various changes may be made in the illustrative methods and compounds without departing from the scope of the present invention. It is intended therefore that the preceding description should be construed as illustrative only and not in a limiting sense.

We claim:

1. A compound of the formula:

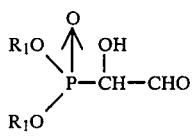

wherein $R_1$ is selected from the group consisting of methyl, propyl, butyl, cyclohexyl, phenyl, benzyl, propyl substituted by chlorine, propyl substituted by bromine, and hydrogen, and in which the $R_1$ groups may be the same or different.

2. The compound of claim 1, wherein $R_1$ is methyl.
3. The compound of claim 1, wherein $R_1$ is isopropyl.
4. A compound of the formula:

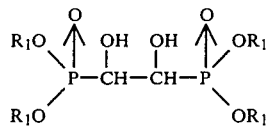

wherein $R_1$ is selected from the group consisting of methyl, propyl, butyl, cyclohexyl, phenyl, benzyl, propyl substituted by chlorine, or propyl substituted by bromine, or in which one of the $R_1$ groups on each phosphinyl moiety is hydrogen, and in which the several $R_1$ groups may be the same or different.

5. The compound of claim 4, wherein $R_1$ is methyl, isopropyl or benzyl, or in which one of the $R_1$ groups on each phosphinyl moiety is hydrogen.
6. The compound of claim 5, wherein $R_1$ is methyl.
7. The compound of claim 5, wherein $R_1$ is isopropyl.
8. The compound of claim 5, wherein $R_1$ is benzyl.
9. 1,2-dihydroxy-1,2-bis(dihydroxyphosphinyl)ethane, having the formula:

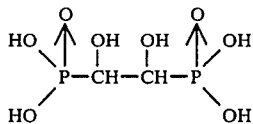

* * * * *